United States Patent [19]

Wickham

[11] 4,237,882
[45] Dec. 9, 1980

[54] NEEDLE SHEATH

[75] Inventor: Ray M. Wickham, Deland, Fla.

[73] Assignee: Sherwood Medical Industries Inc., St. Louis, Mo.

[21] Appl. No.: 79,337

[22] Filed: Sep. 27, 1979

[51] Int. Cl.³ .............................................. A61M 5/00
[52] U.S. Cl. ............................... 128/218 N; 128/221
[58] Field of Search ............... 128/218 R, 218 N, 221, 128/234, 215, 216

[56]  References Cited

U.S. PATENT DOCUMENTS

| 2,911,971 | 11/1959 | Quinche et al. | 128/218 N X |
| 3,721,241 | 3/1973 | Klohr et al. | 128/221 |
| 4,027,669 | 6/1977 | Johnston et al. | 128/218 N |
| 4,121,588 | 10/1978 | Geiger | 128/218 N X |

Primary Examiner—John D. Yasko
Attorney, Agent, or Firm—Wegner, Stellman, McCord, Wiles & Wood

[57] ABSTRACT

A sheath (24) is provided for a syringe (10) having a barrel (18) with a needle assembly (22) projecting axially from the distal end thereof. The needle assembly (22) has a hub (28) with radially projecting ears (62) for threading into a collar (42) on the barrel (18). At least one axially extending, radially projecting rib (60) is carried by the hub (28). The sheath (24) has at least one camming flute (66) comprised of a flat circumferentially facing abutting surface (72) on one side and an axially and circumferentially facing cam surface (74) on the other side thereof. The sheath (24) frictionally grips the needle hub (28) with one rib (60) juxtaposed with respect to the camming flute (66). Rotation of the sheath (24) in one direction will engage the flat surface (72) with the rib (60) to rotate the needle assembly (22) with the sheath (24) for unthreading the needle assembly from the collar (42) on the barrel (18). Rotation of the sheath (24) in the opposite direction engages the rib (60) with the axially facing cam surface to initially thread the hub (28) onto the collar (42) and continued rotation urges the sheath (24) axially relative to the needle assembly (22) to disconnect the sheath (24) from the needle assembly (22).

11 Claims, 7 Drawing Figures

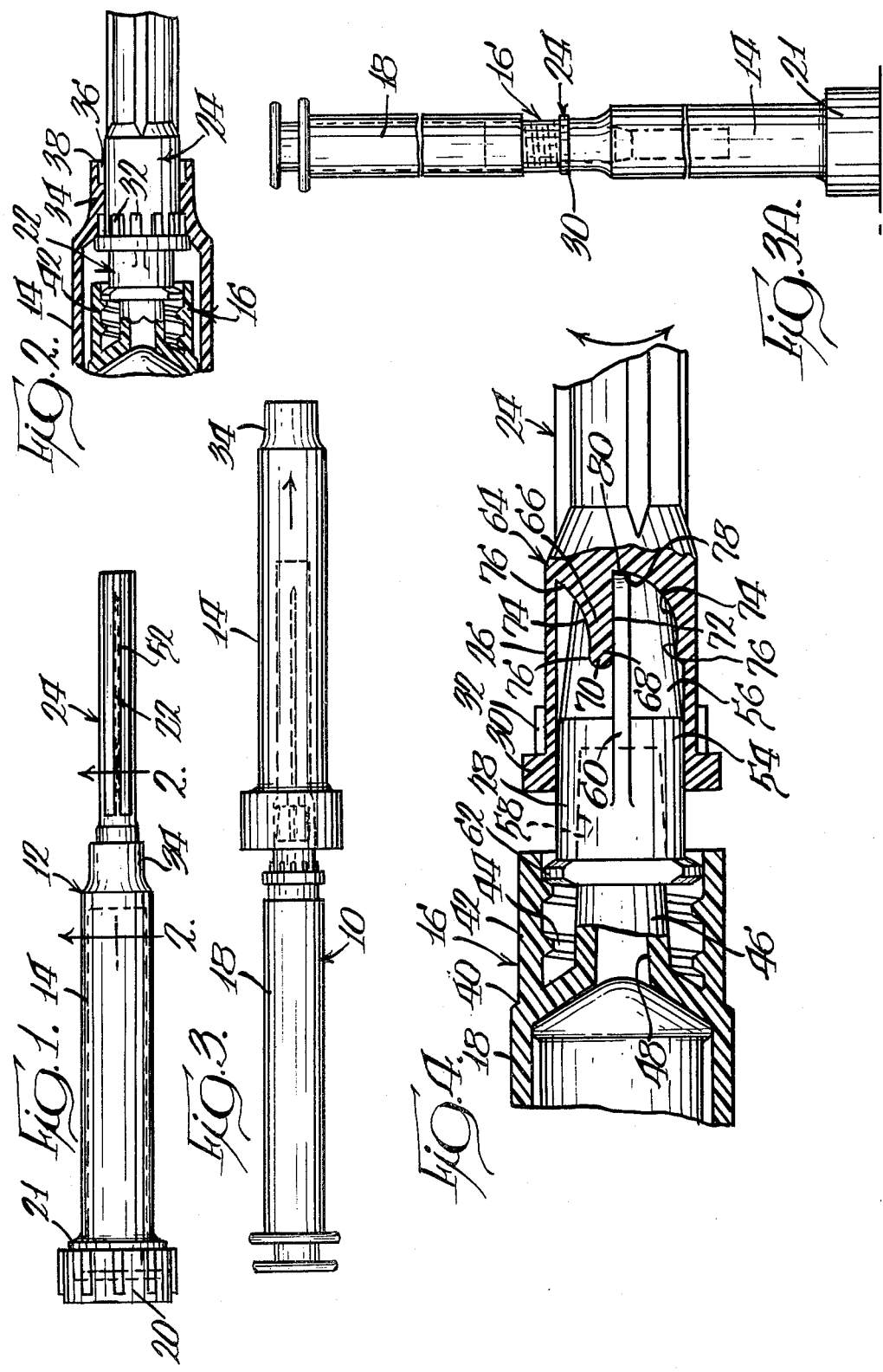

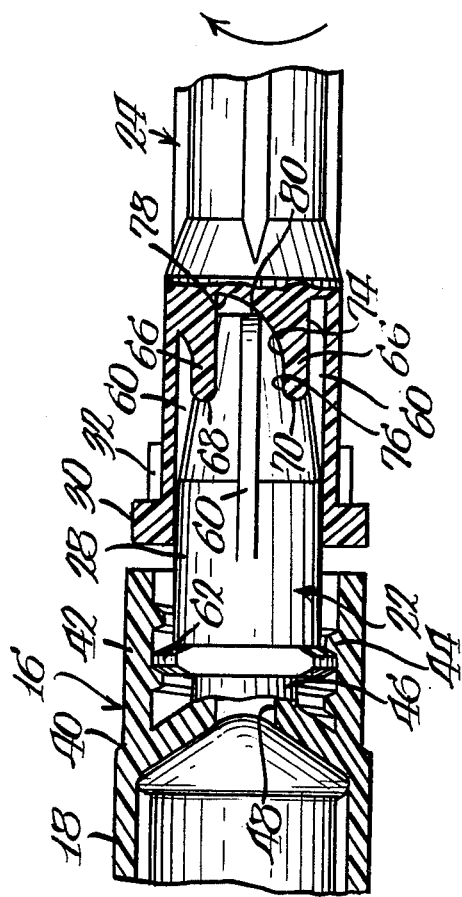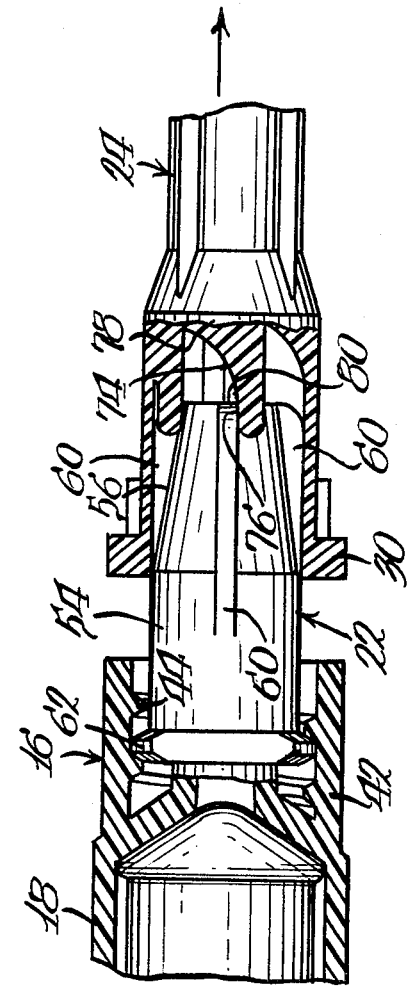

NEEDLE SHEATH

TECHNICAL FIELD

This invention relates to a needle syringe assembly and, more particularly, to a novel sheath wrenching and removing structure for said assembly.

BACKGROUND ART

Needle syringe assemblies are well known and have been continually improved upon through the years. The connection between the needle hub and the barrel of the syringe has received considerable attention in that the connection has to be positive, leak proof, quickly made and relatively simple to complete. The well known luer lock on the distal end of the barrel has resulted which includes a male tapered member and an internally threaded luer lock collar. An early form of needle assembly for use with the barrel of a syringe had a needle and a hub, which hub had a segmented radially extending flange or pair of ears on the proximal end thereof. A sheath was provided which fitted over the needle and frictionally engaged the hub. To connect a needle to the barrel, the sheath was manipulated to align the needle hub with the luer lock collar with the segmented flanges on the hub engaging the threads in the collar. The sheath and needle were rotated to thread the hub onto the barrel and to wedge the tapered luer member in the passage in the hub. The sheath then had to be removed. Frequently the fit between the needle hub and the sheath was so tight that damage was done to the connection or to the needle in trying to remove the sheath. Sometimes the fit between the needle hub and the sheath was too loose so that it was almost impossible to get the grip necessary to properly seat the hub on the tapered luer member. To overcome these problems, ribs were put on the hub and coacting keyways were provided in the sheath so that turning the sheath positively turned the needle hub on the threads in the collar and seated the hub on the tapered luer member. The problem of releasing the sheath from the hub still remained.

DISCLOSURE OF INVENTION

The present invention is directed to overcoming one or more of the problems as set forth above.

According to the present invention, a sheath is provided with a camming means that positively contacts a rib on the hub of the needle assembly so that the sheath and needle assembly will be rotated together in one direction. The camming means has a shaped cam surface which engages with a portion of the rib which will move the sheath axially away from the hub upon the hub sealingly seating on the luer member on the barrel during turning the sheath relative to the needle assembly in a direction opposite to the initially described direction of rotation. The cam surface is of such an extent as to axially move the sheath a sufficient distance relative to the hub as to permit free separation of the sheath from the needle assembly.

The needle syringe assembly may optionally have a sleeve and cap over the barrel of the assembly with the sleeve being axially slid over the sheath to remove the sleeve from the barrel. The distal portion of the sleeve has internal lugs which, upon reversing the sleeve and threading the distal portion over the sheath, engage with mating lugs on the exterior of the sheath to act as a wrench for turning the sheath. In addition, the end of the sleeve forms an enlarged even surface upon which the needle syringe assembly can be stood.

BRIEF DESCRIPTION OF DRAWINGS

FIG. 1 is an assembled view of a sleeve and cap packaged needle syringe assembly having the improved sheath wrenching and camming structure;

FIG. 2 is an enlarged, broken away, partial cross-sectional view taken along the line 2—2 of FIG. 1;

FIG. 3 is a view similar to FIG. 1 only with the sleeve of the package partially removed from the needle syringe assembly;

FIG. 3A is a view showing the distal portion of the sleeve of the package threaded over the needle sheath and engaging with the sheath for simultaneous turning of the sleeve and sheath;

FIG. 4 is an enlarged partial, sectional view of the improved wrenching and camming structure of FIG. 1 with the ribs on the hub contacting the camming flutes on the sheath ready for threading or unthreading the needle assembly from the barrel;

FIG. 5 is a view similar to FIG. 4 only with the sheath rotated clockwise and with the hub seated on the adaptor of the barrel and the rib on the hub riding up the cam surface of the camming flutes; and FIG. 6 is a view similar to FIG. 5 only with the sheath moved axially relative to the needle assembly, ready to be lifted from the assembly in an axial direction.

BEST MODE FOR CARRYING OUT THE INVENTION

Referring to the drawings and, in particular, to FIGS. 1, 2 and 3, thereof, a needle syringe assembly 10 is shown sterile packaged for shipment and storage. The package 12 is comprised of a sleeve 14 telescoping over a connector 16 and a syringe barrel 18. The package 12 includes a cap 20 sealed over the open enlarged proximal end portion 21 of the sleeve 14. The barrel 18 has a needle assembly 22 removably connected to the distal end portion thereof by means of the connector 16. A cover or needle sheath 24 telescopes over the needle assembly 22 and has a proximal end portion 26 frictionally engaging the outer surface of the needle hub 28 of the needle assembly 22. The exterior of the proximal portion 26 of the sheath 24 has an enlarged flange 30 with a plurality of circumferentially spaced apart lugs 32 projecting radially out from the sheath 24 and integral with the one axial face of the flange 30. As can best be seen in FIG. 2, the distal portion 34 of the sleeve 14 has internal, circumferentially spaced lugs 36 which extend radially inward from the distal portion 34 and extend axially inward from a distal end 38 of said distal portion 34 of the sleeve 14.

The cap 20 is turned relative to the sleeve 14 to break the sterile seal, whereupon the sleeve 14 can be removed axially relative to the barrel 18, such as is shown in the action view of FIG. 3. Sleeve 14 can then be discarded along with the cap 20, or can be reversed and the distal portion 34 can be threaded over the needle sheath 24 until the lugs 36 interfit with the lugs 32 on the sheath 24. The unit can then be stood on end with the enlarged proximal end portion 21 of the sleeve 14 serving as a stable base with plunger head 37 and the barrel 18 projecting upwardly into a readily graspable position for a doctor, nurse, or the like.

The barrel 18, at the distal end portion 40 thereof, has a luer lock collar 42 containing internal threads 44.

Centrally disposed in the collar 42 and communicating through passage 48 with the interior of the barrel 18 is a tapered male luer member 46. The needle assembly 22 is comprised of the hub 28 and an axially extending needle 52 affixed thereto. The hub 28 has a cylindrically shaped proximal end portion 54 which integrally joins with a tapered hub portion 56 which supports and stabilizes the proximal portion of the needle 52. The hub 28 has an internal aperture 58 opening proximally thereof which is adapted to receive the male leur member 46 in telescoping relationship and, at the appropriate position, will seat against the male luer member 46 to seal the needle assembly 22 to the barrel 18. One or more ribs 60 extend axially along the outer surface of the tapered portion 56 of the hub 28 and, since the cylindrical portion 54 of the hub 28 has a slight taper toward the needle end, the ribs 60 will merge into the proximal portion 54 just beyond the middle of the portion 54. The proximal portion 54 of the hub 28 has two or more radially outwardly extending segmented flanges or ears 62 which, in the illustrated form, may have a cross-sectional shape resembling a male thread. The ears 62 on the hub 28 are adapted to fit into the luer lock collar 42 so that upon turning the needle assembly 22 relative to the barrel 18, the ears 62 will advance on the threads 44 to positively engage the walls of the aperture 58 in the hub 28 on the tapered male luer member 46.

An improved wrenching and camming structure 64 is provided, in one preferred form, on the interior of the proximal end portion 26 of the sheath 24. Specifically, one or more camming flutes 66 are formed on the internal surface of the sheath 24 with each flute 66 comprising a radially inwardly extending member 68 having a rounded projecting tip 70 on the axially outward facing end thereof. A flat wrenching surface 72, which extends substantially parallel to the axis of the sheath 24, faces circumferentially on one side of the flute 66. The circumferentially opposite side of the flute 66 has a curved camming surface 74 which forms an arc from the projecting tip 70 where an axially extending portion 76 lies substantially parallel to the axis of the sheath 24 to a portion 78 which extends substantially peripherally of the sheath 24. In the illustrated embodiments of FIGS. 4, 5 and 6, the hub 28 has four ribs 60 and the sheath 24 has a mating number of camming flutes 66, with one camming flute 66 operatively associated with one rib 60. The axially facing distal end 80 of each rib 60 engages with the peripheral portion 78 of the curved camming surface 74 of one camming flute 66 such that the proximal face of the flange 30 on the sheath 24 will be spaced from the distal end of the luer lock collar 42 when the ears 62 just engage in the opening of the collar 42 (FIG. 4). The flange 30 on the sheath 24 should be spaced a sufficient distance from the ears 62 that when the ears 62 are threaded as far into the luer lock collar 42 as is necessary to seat the walls of the aperture 58 on the tapered male luer member 46, there will still be a short distance between the flange 30 and the distal end of the collar 42. There should be no contact between the flange 30 and the end of the collar 42.

INDUSTRIAL APPLICABILITY

When it is desired to seat the needle assembly 22 on the barrel 18, as is shown in FIG. 4, the rib 60 has the end 80 nested in the bottom of the camming surface 74 and the ears 62 are on the initial thread 44 in the collar 42. The sheath 24 is rotated in a clockwise direction relative to the barrel 18 whereupon the sheath 24 will initially grip the hub 28, and the end 80 will nest in the bottom of the camming surface 74 with sufficient force to thread the ears 62 of the hub 28 into the thread 44 of the luer collar 42. When the walls of the aperture 58 seat on the male luer member 46, the hub 28 will stop rotating, whereupon further rotational force on the sheath 24 will cause the ends 80 of the ribs 60 to ride up the camming surface 74 which will move the sheath 24 axially relative to the hub 28 to an intermediate position as shown in FIG. 5. Continued rotation of the sheath 24 relative to the stationary hub 28 will cause the ribs 60 to move all the way up the camming surface 74 to the axially extending portion 76, as is shown in FIG. 6, which will have forced the sheath 24 axially to a point where the internal diameter of the sheath 24 will be greater than the external diameter of the encompassed hub 28 of the needle assembly 22 so that free axial movement of the sheath 24 relative to the needle assembly 22 is possible. The needle syringe assembly 10 is now ready for use.

To re-sheath the needle 52 and to remove the needle assembly 22 from the barrel 18, the sheath 24 is telescoped over the needle 52 until the ribs 60 engage the camming surface 74 and ride down the camming surface 74 until the ends 80 of the ribs 60 are against portion 76 in the lowermost or bottom portion of the camming surface 74. The ribs 60 will now abut the flat wrenching surface 72 of the camming flutes 66. Counterclockwise rotation of the sheath 24 will urge the camming flutes 66 against the flat of the ribs 60 to turn the needle assembly 22 relative to the barrel 18 to back the ears 62 out of the luer lock collar 42 and disengage the tapered aperture 58 from the tapered male luer member 46. The needle assembly 22 is now removed from the barrel 18 and is sheathed in the sheath 24 for ready disposal.

With the improved wrenching and camming structure 64, the sheath 24 is readily broken loose from the needle assembly 22 after the needle assembly 22 is seated on the barrel 18, so as to prevent strains, stresses and breakage of the needle assembly 22 and/or barrel 18. The same camming arrangement can be used to remove the needle assembly 22 from the barrel 18 and can be used to secure the needle assembly 22 to the barrel 18 prior to separation of the sheath 24 from the needle assembly 22.

Although the description has proceeded with the camming flutes 66 on the inside of the sheath 24 and the ribs 60 are on the needle hub 28, it is understood that these parts may be reversed in direction and location without departing from the invention.

Other aspects, objects and advantages of this invention can be obtained from a study of the drawings, the disclosure and the appended claims.

What is claimed is:

1. A needle sheath (24) for a syringe (10) having a barrel (18), a connector (16) on the distal end of said barrel (18), and a needle assembly (22) removably connectable to said barrel (18), said needle sheath (24) encircling a portion of said needle assembly (22), and comprising: cam means (64) operative between said needle sheath (24) and said needle assembly (22) for forcing said needle sheath (24) axially relative to said needle assembly (22) upon rotating said sheath (24) relative to said needle assembly (22) whereby said needle sheath (24) is separated from said needle assembly (22).

2. A needle sheath (24) as claimed in claim 1 wherein said cam means (64) comprises at least one camming flute (66) carried internally on said needle sheath (24) and a cam follower means (60) carried by said needle assembly (22), an axially facing curved camming surface (74) on said camming flute (66), said cam follower means (60) engaging with said camming surface (74) and riding up the curve of said camming surface (74) upon relative rotation between the needle sheath (24) and the needle assembly (22) to urge the needle sheath (24) axially relative to said needle assembly (22).

3. A needle sheath (24) as claimed in claim 1 wherein said needle assembly (22) includes a hub (28) at the proximal end portion thereof, axially extending, radially projecting ears (62) on said hub (28), camming flutes (66) on the internal surface of said needle sheath (24), a curved camming surface (74) on one circumferentially facing side of each flute (66) and a flat blocking surface (72) on the opposite circumferentially facing side thereof, one of said projecting ears (62) engaging said flat blocking surface (72) to rotate said needle assembly (22) with said needle sheath (24) in one direction of rotation of said needle sheath (24), and said one projecting ear (62) riding up said curved camming surface (74) to move said needle sheath (24) axially relative to said needle assembly (22) upon rotation of said needle sheath (24) in the opposite direction.

4. In a needle sheath (24) for a syringe (10) having a barrel (18), a luer lock connector (16) on the distal end (40) of said barrel (18), and a needle assembly (22) removably connected to said luer lock connector (16), said needle assembly (22) including a needle (52) axially extending from a hub (28) having axially extending radially projecting ribs (60) on the outer periphery thereof, and a needle sheath (24) encasing said needle (52) and frictionally engaging said hub (28), in combination: cam means (64) carried by said needle sheath (24) and engaging with said ribs (60) on said needle assembly (22), said cam means (64) comprising a camming flute (66) having a cam surface (74) on one side and a flat surface (72) on the opposite side thereof, said flat surface (72) contacting one of said ribs (60) upon rotating said needle sheath (24) in one direction to rotate the needle assembly (22) with said needle sheath (24) for removing said needle assembly (22) from said connector (16), and upon rotating said needle sheath (24) in a direction opposite to said first-named direction said cam surface (74) will contact one of said ribs (60) to initially rotate said needle sheath (24) and said needle assembly (22) together relative to the barrel (18) to connect said needle assembly (22) to said connector (16) and thereafter to move the needle sheath (24) axially relative to said needle assembly (22) for removing said needle sheath (24) from said needle assembly (22).

5. In a needle sheath (24) as claimed in claim 4 wherein said cam surface (74) is curved and has one portion (76) parallel to an axis of the sheath (24) and has a second portion (78) tangent to a circle in the hub (28) defining the distal end of said camming flute (66).

6. In a needle sheath (24) as claimed in claim 4 wherein a plurality of camming flutes (66) are provided in the sheath (24) and a flat surface (72) of each flute (66) engages with one of said ears (62) on said hub (28).

7. A needle syringe assembly (10) having a barrel (18) with a threaded collar (42) encircling a tapered luer connector (46) on one end thereof, a needle assembly (22) having a hub member (28) with ears (62) engaging said threaded collar (42), said hub member (28) having an aperture (58) with walls engaging with said tapered luer member (46), a needle sheath member (24) encasing said needle assembly (22), said needle sheath member (24) and said hub member (28) of the needle assembly (22) having interfitting means (64) for wrenching said hub member (28) onto said barrel (18) and for camming said sheath member (24) free from said hub member (28), said interfitting means (64) comprising camming flutes (66) carried by one of said members (24,28) and having a flat surface (72) on one side and a curved camming surface (74) on the other side thereof, ribs (60) carried by said other member (24,28) and having at least one rib (60) engaging selectively with said flat surface (72) and with said camming surface (74) whereby rotating said sheath member (24) in one direction engages at least one of said ribs (60) with at least one of said flat surfaces (72) to rotate the hub member (28) relative to the barrel (18) to unthread the hub member (28) from the barrel (18) and rotating said sheath member (24) in the opposite direction initially rotates the ears (62) on the hub member (28) into the collar (42) and subsequently at least one of said ribs (60) engages with at least one of said curved cammed surfaces (74) to urge the sheath member (24) axially away from the hub member (28) to separate the sheath member (24) from the needle assembly (22).

8. A needle syringe assembly (10) as claimed in claim 7 wherein said camming flutes (66) are on said sheath member (24) and said ribs (60) are on said hub member (28).

9. A needle syringe assembly (10) as claimed in claim 7 wherein said interfitting means (64) comprises four camming flutes (66) and four ribs (60).

10. A needle syringe assembly (10) as claimed in claim 7 wherein a closed end sleeve (14) has internal lugs (36) which engage with external lugs (32) on said sheath member (24) when said sleeve (14) is telescoped over said sheath member (24), said sleeve (14) serving as an enlarged gripping member for turning said sheath member (24) and serving as a support for said needle syringe assembly (10) when stood on end.

11. A method of assembling a needle assembly (22) on a barrel (18) of a syringe wherein said barrel (18) has an internally threaded collar (42) and a tapered luer lock member (46), grasping a sheath (24) encasing a needle (52) of said needle assembly (22) and turning said sheath (24) to thread a hub (28) of the needle assembly (22) into said collar (42) and onto said tapered luer lock member (46), continued turning of the sheath (24) will engage ribs (60) on the hub (28) with a curved camming surface (74) on the sheath (24) to urge the sheath (24) axially relative to the hub (28) to expose the needle (52) for use.

* * * * *